United States Patent [19]

Frese et al.

[11] Patent Number: 4,468,622
[45] Date of Patent: Aug. 28, 1984

[54] GRADIENT COIL SYSTEM FOR NUCLEAR MAGNETIC RESONANCE APPARATUS

[75] Inventors: Georg Frese; Horst Siebold, both of Erlangen, Fed. Rep. of Germany

[73] Assignee: Siemens Aktiengesellschaft, Munich, Fed. Rep. of Germany

[21] Appl. No.: 406,455

[22] Filed: Aug. 9, 1982

[30] Foreign Application Priority Data

Aug. 27, 1981 [DE] Fed. Rep. of Germany ....... 3133933

[51] Int. Cl.$^3$ .............................................. G01R 33/08
[52] U.S. Cl. .................................... 324/319; 324/318
[58] Field of Search .............................. 324/318–320, 324/300

[56] References Cited

U.S. PATENT DOCUMENTS

| | | | |
|---|---|---|---|
| 3,566,255 | 2/1971 | Jaynes | 324/320 |
| 3,569,823 | 3/1971 | Golay | 324/320 |
| 3,577,067 | 5/1971 | Weaver | 324/320 |

FOREIGN PATENT DOCUMENTS

| | | | |
|---|---|---|---|
| 21535 | 1/1981 | European Pat. Off. | |
| 2840178 | 3/1980 | Fed. Rep. of Germany | |

Primary Examiner—Michael J. Tokar
Attorney, Agent, or Firm—Kenyon & Kenyon

[57] ABSTRACT

A gradient coil system for an image-generating, nuclear magnetic resonance tomographic apparatus, particularly a zeugmatographic apparatus. The gradient coil system is arranged on a support body of rotational symmetry, illustratively a hollow cylindrical support body, having an axis which extends along the z-direction of an x, y, z coordinate system which has an origin in the center of an imaging region. The gradient coil system contains two pairs of toroidal individual coils which are arranged symmetrically with respect to an x-y plane which extends through the center of the imaging region and which are arranged perpendicular to the z-axis. The direction of current flow in the individual coils of a coil pair is opposite to the direction of flow in the individual coils of the other coil pair. Moreover, further sets of coils are provided for generating field gradient $G_x$ in the x-direction, and $G_y$ in the y-direction. The hollow cylindrical shape of the support body on which the individual coils are arranged permit an imaging region having a substantially spherical volume with a substantially constant field gradient $G_z$ to be achieved. Each of the coils has a predetermined linkage factor which corresponds to the product of the current flowing through the number of coil turns of the coil. Those coils which are arranged further from the plane of symmetry have a substantially larger linkage factor than the coils which are nearer to the plane of symmetry.

8 Claims, 1 Drawing Figure

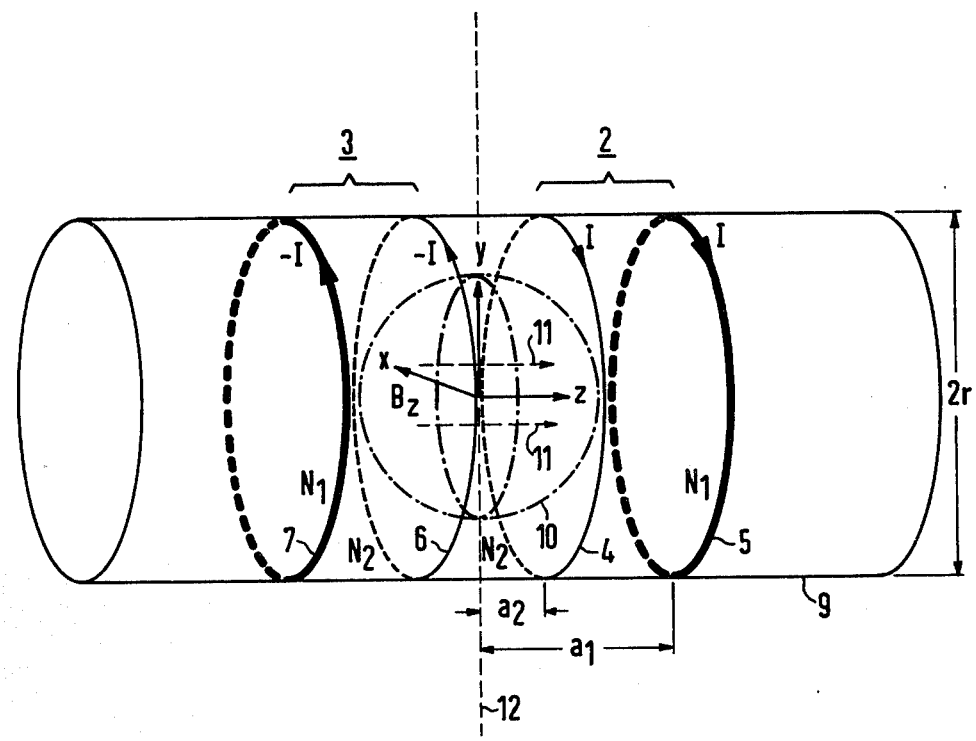

GRADIENT COIL SYSTEM FOR NUCLEAR MAGNETIC RESONANCE APPARATUS

BACKGROUND OF THE INVENTION

This invention relates generally to gradient field coil systems for image-generating apparatus which is used in nuclear magnetic resonance tomography, and more particularly, to an arrangement where a gradient coil system is arranged on at least one rotation-symmetrical support body having an axis which is arranged in the z-direction and which has a field gradient which is essentially constant in the imaging region.

In image-generating apparatus for nuclear magnetic resonance technology, particularly for zeugmatography, a gradient field coil system is arranged on a rotation-symmetrical support body for producing in the imaging area a largely constant field gradient $G_z = \delta B_z/\delta z$. This substantially constant field gradient is produced by a respective pair of toroidal individual coils which are at least approximately symmetrical to the x-y plane through the center of the imaging area and which extends in a direction perpendicular to the z-axis. Current flows in opposite directions through the toroidal coils of the pair. A further set of individual coils is arranged substantially symmetrically with respect to the plane of symmetry for generating field gradient $G_x = \delta B_z/\delta x$ in the x-direction, which field gradient is essentially constant in the imaging area, and at least a still further set of individual coils for generating a corresponding field gradient $G_y = \delta B_z/\delta y$ in the y-direction. Such a gradient coil system is described in DE-OS No. 28 40 178.

In the field of medical diagnostics, imaging methods have been proposed wherein an image similar to an x-ray tomogram is constructed by numerical or measurement analysis of integrated proton resonance signals from the spatial spin density and/or relaxation time distribution of a human body to be examined. The corresponding method is also known as "zeugmatography" or nuclear spin tomography. See: "Nature", volume 242 1973, pages 190 to 191.

According to the known methods of nuclear spin tomography, three different kinds of coil systems are required, in principle. One magnet is required to generate a stationary base field $B_z$ which must be as homogeneous as possible and have an order of magnitude of between 0.05 to 0.5 Tesla. Magnetic field $B_z$ is assumed to be oriented, for example, in the z-direction of an orthogonal x, y, z coordinate system. Moreover, the z-direction is the examination axis along which a body, particularly a human body to be examined, is placed in the magnetic field. The coordinate origin is to be situated in the imaging, or examination region. Furthermore, a high-frequency coil arrangement is to be provided for the corresponding precession frequency of the nuclear spin to be considered, in order to excite the nuclear spin, and optionally, to receive the induction signals. If the high-frequency coil arrangement is used for detecting these signals, a separate receiving coil system may also be provided. Finally, a system of gradient coils is needed which generate a preferably orthogonal set of supplementary fields $G_z = \delta B_z/\delta z$; $G_x = \delta B_z/\delta x$; and $G_y = \delta B_z/\delta y$. These supplementary fields are small in comparison with the base field $B_z$ which is oriented in the z-direction. Only the gradient fields which are switched on in the predetermined sequence permit a distinction in the location due to the shape of the precession frequency of the nuclei. See, for example, "Journal of Magnetic Resonance", volume 18, 1975, pages 69 to 83; volume 29, 1978, pages 355 to 373.

If the gradients $G_x$, $G_y$, and $G_z$ in an imaging region are not constant to a high degree, but are still functions of the location itself, blurred, distroted, and artificial images are generated. Linearity of the gradient fields and the constancy of their derivatives $G_x$, $G_y$, and $G_z$ in the imaging region are therefore an essential condition for high image quality of nuclear spin tomographic apparatus.

Generally, the three gradients can be generated by magnetic quadrupoles. The fact that the coils for generating the gradients must be arranged inside the base field magnet must be taken into consideration in the design of nuclear spin resonance apparatus. Thus, sufficient space must be left for placing the human body to be examined.

An analytic derivation of the geometry of such coil systems can be obtained from the U.S. Pat. No. 3,569,823. Thus, the coils in the coil system are to produce a magnetic field which is developed into spherical functions which are as pure as possible. It is assumed here that the field-generating conductors are arranged on the outside and/or inside cylindrical surfaces of a hollow cylindrical support body. In such an arrangement, disturbances of the main spherical functions which are generated by the finite length of the conductors and their locations are analytically minimized.

The hollow cylindrical support body with the corresponding gradient coils can be inserted into a field magnet having an axis which coincides with the axis of the base magnet and which points, for example, in the z-direction of an orthogonal x, y, z coordinate system. The z-gradient $G_z$ is generated by two ring coils through which current flows in opposite directions. In order to generate the x-gradient $G_x$ two saddle-shaped coil pairs are placed on the support body. For the y-gradient $G_y$, a corresponding system of four saddle-shaped coils is provided which are arranged opposite to the x-gradient coils either on the outer or inner cylindrical surfaces of the cylindrical support body, shifted by 90° in the circumferential direction. The two pairs of individual coils of each coil set are arranged symmetrically with respect to an x-y plane which is oriented perpendicularly to the cylinder axis and extends through the center of the imaging region.

This linearity requirement can be met to a high degree by the coil arrangement described in the aforementioned DE-OS No. 28 40 178 or the published European Patent Application EP No. 21 531 A1. To this end, the gradient coil system of the known magnet coil arrangement is not arranged on a hollow cylindrical support body, but rather on a support body having a spherical shape. The examination axis corresponds to the axis of rotation of the support body, and extends in the z-direction of an orthogonal x, y, z coordinate system where the coordinate origin is placed in the center of the examination or imaging region. Instead of utilizing two toroidal individual coils for generating the field gradient $G_z$ in accordance with U.S. Pat. No. 3,569,823, a pair of toroidal individual coils is arranged at least substantially symmetrical with respect to the x-y plane through the center of the imaging region. The direction of current flow in the individual coils of one pair is opposed to the current flow direction in the individual coils of the other pair. In this arrangement, each of the z-gradient coils must have the same number of turns.

It is a problem with this arrangement, however, that the manufacture of such individual coils on the surface of a support body having a spherical shape is relatively expensive. The coils must be arranged on coordinates which must be positioned extremely accurately with respect to the coordinate origin so that the required linearity conditions can be met.

It is, therefore, an object of this invention to provide a gradient coil system which can be simply and inexpensively manufactured.

It is a further object of this invention to provide a gradient coil system which contains all of the advantages of the hollow cylindrical support body which is known in the art.

SUMMARY OF THE INVENTION

The foregoing and other objects are achieved by this invention which provides a gradient coil system for an image-generating device of a nuclear magnetic resonance apparatus; the gradient coil system being arranged on at least one rotation-symmetrical support body in the form of a hollow cylinder having a predetermined radius r. The hollow cylindrical support body has an axis which extends in the z-direction of an orthogonal x, y, z coordinate system, the coordinate system having an origin in the center of an imaging area. A base field magnet is provided for producing a magnetic field $B_z$ along the z-direction, the magnetic field of the gradient coil system having a substantially constant field gradient $G_z \delta B_z / \delta z$. A pair of toroidal individual coils are arranged substantially symmetrically with respect to a x-y plane of symmetry which extends through the center of the imaging region perpendicular to the z-axis. The direction of current flow in the individual coils of the pair of coils is in opposite directions, for generating field gradients $G_x = \delta B_z / \delta x$. A further set of individual coils is provided for generating field gradients $G_y = \delta B_z / \delta y$ in the y-direction. The individual coils of the coil pairs which generate field gradient $G_z$ are arranged at predetermined distances from the plane of symmetry. Moreover, an electric linkage factor which corresponds to the product of the current flowing through the coils and its respective number of turns is greater for individual ones of the coils which are further away from the plane of symmetry than for those coils which are nearer the plane of symmetry.

It is a feature of this invention that a linearity region can be achieved with the z-gradient coils which extends in three dimensions. The geometric dimensions of the individual coils can be kept small in order to limit the current requirement and the inductance of the coils. The gradient fields can then be switched on and off in short time intervals.

BRIEF DESCRIPTION OF THE DRAWING

Comprehension of the invention is facilitated by reading the following detailed description in conjunction with the annexed drawing which schematically depicts the z-gradient coils of an image-generating apparatus constructed in accordance with the principles of the invention.

DETAILED DESCRIPTION

In known apparatus for the practice of nuclear magnetic resonance technology, illustratively nuclear spin tomography or zeugmatography, a known magnetic coil system such as is described in U.S. Pat. No. 3,569,823, is used to provide a base magnet field. The present inventive gradient coil system may be used to improve the known arrangement which comprises at least one normal conducting, or superconducting, field coil system arranged concentrically with respect to the z-axis of an orthogonal x, y, z coordinate system. The known magnet coil arrangement generates a homogeneous magnetic base field in the z-direction. Furthermore, gradient coils for generating constant magnetic field gradients in an imaging region. The origin of the x, y, z coordinate system is located in the center of the imaging region. The magnet coils are arranged so that the center of the homogeneous field region is accessible along the axial direction to permit, for example, a human body which is to be examined to be placed in the magnetic field along the z-axis. Nuclear spin is excited by means of a high-frequency field which is directed perpendicular to the z-axis. The high-frequency field is generated by coils which also serve as receiver coils for receiving the nuclear spin resonance signals.

The gradient coil system according to the invention, which may be used in apparatus for the practice of nuclear magnetic resonance technology, is comprised of z-gradient coils having a particular design which can be seen from the drawing. The gradient coils for generating linear field gradients $G_x$ and $G_y$, in the x and y directions, are not shown in the figure, and may be coils of the type which are known from U.S. Pat. No. 3,569,823; DE-OS No. 28 40 178; or European Patent application EP No. 21 535 A1.

The z-gradient coil system which is schematically shown in the drawing in an oblique view is comprised of two pairs of coils 2 and 3. Conductor portions which are not normally visible in this view are indicated in phantom by dashed lines. Each coil pair 2 and 3 is provided with two individual coils 4 and 5, and 6 and 7, respectively, which are arranged on the outer and/or inner surfaces of a hollow cylindrical support body 9, the outside or inside radius of which has a magnitude r. The axis of the cylinder is oriented in the z-direction of an orthogonal x, y, z coordinate system. The z-axis is also the examination axis, alnog which a body to be examined can placed in the examination, or imaging, region 10 which is indicated by dash-dotted lines. In this region, a base field magnet which is indicated by dashed arrows 11 produces a magnetic field $B_z$ which is substantially homogeneous and oriented in the z-direction. The coordinate origin of the x, y, z coordinate system is located at the center of the imaging region.

The two coil pairs 2 and 3 are arranged symmetrically with respect to an x-y plane which extends through the center of the imaging region. This plane of symmetry is indicated by a dashed line 12. The direction of current flow which is indicated by the arrows at the ring-shaped individual coils are opposed to one another in the individual coils 4 and 5 of coil pair 2, and in coils 6 and 7 of the other coil pair 3.

In order to ensure sufficient linearity of the z-gradient fields, individual coils 4 to 7, through which currents I and $-I$, respectively, flow are arranged at predetermined distances from the plane of symmetry through the coordinate origin. In addition a substantially larger linkage factor is chosen for the outer individual coils 5 and 7, which are further removed from the plane of symmetry and have a number of turns $N_1$, than for individual coils 4 and 6 which are near the plane of symmetry, and are provided with a number of turns $N_2$.

In this disclosure, such linkage is understood to mean the product of the current I and the number of turns N of a coil. This product is also called "ampere turns."

The distance $a_1$ of the outer individual coils 5 and 7 from the plane of symmetry 12 has a value which is advantageously selected to be between 0.9r and 1.3r. Preferably, a vlaue of 1.1r is selected. The distance $a_2$ of individual coils 4 and 6 from the plane of symmetry depends upon the value of distance $a_1$, and is advantageously selected to be between $0.25a_1$ and $0.5a_1$. This value is preferably selected to be approximately $0.33a_1$.

As noted, a current having a value I flows through individual turns $N_1$ and $N_2$ of coils 5, 7, and 4, 6. An electric linkage factor $I \times N_2$ is selected for individual coils 4 and 6, and a linkage factor $I \times N_1$ for individual coils 5 and 7. The linkage factor of coils 5 and 7 is at least three times larger than that of coils 4 and 6 which are closer to the plane of symmetry. In one advantageous embodiment, the ratio $(I \times N_1):(I \times N_2)$ is selected to be between 6:1 and 12:1. A ratio of approximately 9:1 is preferred.

With respect to the specific illustrative embodiment, it was assumed that the magnitude of the current I through the four indivdual coils 4 and 7 is the same and only the number of turns $N_1$ and $N_2$ are different. However, it is equally possible to adjust the currents in the coils differently so as to obtain the predetermined values for the electric linkage through these coils.

For the mentioned values of distances $a_1$ and $a_2$, and linkage $I \times N_1$ and $I \times N_2$, an imaging region 10 is achieved having a largely constant field gradient $G_z$ which has a approximately spherical shape with a radius of approximately $(\frac{2}{3})r$.

Although the invention has been described in terms of specific embodiments and applications, persons of skill in the art, in light of this teaching, can generate additional embodiments without exceeding the scope or departing from the spirit of the claimed invention. Accordingly, it is to be understood that the drawings and descriptions in this disclosure are proffered to facilitate comprehension of the invention and should not be construed to limit the scope thereof.

What is claimed is:

1. A gradient coil system for an image-generating, nuclear magnetic resonance tomographic apparatus, the gradient coil system is arranged on at least one rotation-symmetrical support body, having an axis which extends along the z-direction of an orthogonal x, y, z coordinate system, the coordinate system having an origin located at the center of an imaging region, the system having a base field magnet for producing a magnet field $B_z$ in the z-direction, the magnet field of said gradient coil system having a field gradient $G_z = \delta B_z/\delta z$ which is essentially constant in the imaging region, the system further having at least two toroidal individual coils arranged symmetrically with respect to an x-y plane of symmetry through the center of the imaging region for conducting current in opposite directions, at least one set of individual coils arrnaged substantially symmetrically with respect to the plane of symmetry for generating a field gradient $G_x = \delta B_z/\delta x$ in the x-direction, which field gradient being substantially constant in the imaging area, and at least one further set of individual coils for generating a further corresponding field gradient $G_y \times \delta B_z/\delta y$ in the y-direction, the gradient coil system being characterized in that the rotation-symmetrical support body has the form of a hollow cylinder having a predetermined radius r, the toroidal individual coils for generating the field gradient $G_z$ are arranged at predetermined distances from the plane of symmetry and each such individual coil has a corresponding linkage factor wherein selected ones of the coils which are further away from the plane of symmetry than others of the coils have substantilly larger linkage factors than said other coils which are nearer to the plane of symmetry.

2. The gradient coil system of claim 1 wherein the selected ones of the coils which are further from the plane of symmetry are disposed at a distance therefrom which is between 0.9r and 1.3r.

3. The gradient coil system of claim 2 wherein the selected ones of the coils which are further from the plane of symmetry are arranged at a distance which is approximately 1.1r.

4. The gradient coil system of claim 1 wherein the selected ones of the coils which are arranged further from the plane of symmetry are disposed at a distance a 1 from the plane of symmetry and the others of the coils which are arranged nearer to the plane of symmetry are disposed at a distance $a_2$ from the plane of symmetry, said coils which are closer to the plane of symmetry being disposed at a distance which is between $0.25a_1$ and $0.5a_1$.

5. The gradient coil system of claim 4 wherein said others of the individual coils which are disposed closer to the plane of symmetry are arranged at approximately $0.33a_1$.

6. The gradient coil system of claim 1, 2, 3, 4, or 5 wherein the linkage factor of the selected ones of the coils which are further away from the plane of symmetry is between six times and twelve times greater than the linkage factor of the individual coils which are closer to the plane of symmetry.

7. The gradient coil system of claim 6 wherein the linkage factor of the coils which are further away from the plane of symmetry is approximately nine times larger than the linkage factor of those coils which are nearer to the plane of symmetry.

8. The gradient coil system of claim 6 wherein said coils which are further from the plane of symmetry are adapted to conduct a current which is different in magnitude from a current which the coils which are nearer to the plane of symmetry are adapted to conduct.

* * * * *

UNITED STATES PATENT AND TRADEMARK OFFICE
CERTIFICATE OF CORRECTION

PATENT NO. : 4,468,622
DATED : August 28, 1984
INVENTOR(S) : Georg Frese and Horst Siebold It is certified that error appears in the above-identified patent and that said Letters Patent is hereby corrected as shown below:

Column 1, line 41, insert --,-- (comma) after "volume 242";

line 64, change "32" to --=-- (equal sign).

Column 2, line 6, change "distroted" to --distorted--.

Column 3, line 22, change "supprot" to --support--;

line 31, insert --=-- (equal sign) after "$G_z$".

Column 4, line 43, change "alnog" to --along--.

Column 5, line 7, change "vlaue" to --value--.

Claim 1, line 16, change "arrnaged" to --arranged--;

line 22, change "X" (multiplication sign) to --=-- (equal sign).

Signed and Sealed this

Twelfth Day of March 1985

[SEAL]

Attest:

DONALD J. QUIGG

Attesting Officer     Acting Commissioner of Patents and Trademarks